United States Patent [19]
Kónya et al.

[11] Patent Number: 6,146,396
[45] Date of Patent: Nov. 14, 2000

[54] DECLOTTING METHOD AND APPARATUS

[75] Inventors: András Kónya; Kenneth C. Wright, both of Houston, Tex.

[73] Assignee: Board of Regents, The University of Texas System, Austin, Tex.

[21] Appl. No.: 09/262,994

[22] Filed: Mar. 5, 1999

[51] Int. Cl.$^7$ .................................................. A61M 29/00
[52] U.S. Cl. .......................................... 606/159; 606/200
[58] Field of Search .............................. 606/1, 108, 198, 606/200, 159; 604/104, 105

[56] References Cited

U.S. PATENT DOCUMENTS

| | | |
|---|---|---|
| 3,540,431 | 11/1970 | Mobim-Uddim . |
| 3,794,041 | 2/1974 | Frei et al. . |
| 3,868,956 | 3/1975 | Alfidi et al. . |
| 4,365,632 | 12/1982 | Kortum . |
| 4,425,908 | 1/1984 | Simon . |
| 4,447,227 | 5/1984 | Kotsanis . |
| 4,494,531 | 1/1985 | Gianturco . |
| 4,512,338 | 4/1985 | Balko et al. . |
| 4,619,246 | 10/1986 | Mølgaard-Nielsen et al. . |
| 4,638,803 | 1/1987 | Rand . |
| 4,650,466 | 3/1987 | Luther . |
| 4,762,130 | 8/1988 | Fogarty et al. ......................... 606/159 |
| 4,832,055 | 5/1989 | Palestrant . |
| 4,921,484 | 5/1990 | Hilstead .................................. 606/159 |
| 4,957,501 | 9/1990 | Lahille et al. . |
| 4,994,069 | 2/1991 | Ritchart et al. . |
| 4,997,435 | 3/1991 | Demeter . |
| 5,053,008 | 10/1991 | Bajaj . |
| 5,071,407 | 12/1991 | Termin et al. . |
| 5,104,404 | 4/1992 | Wolff . |
| 5,108,407 | 4/1992 | Geremia et al. . |
| 5,108,419 | 4/1992 | Reger et al. . |
| 5,133,733 | 7/1992 | Rasmussen et al. . |
| 5,217,484 | 6/1993 | Marks . |
| 5,256,146 | 10/1993 | Ensminger et al. . |
| 5,263,964 | 11/1993 | Purdy . |
| 5,334,210 | 8/1994 | Gianturco . |
| 5,350,398 | 9/1994 | Pavcnik et al. . |
| 5,370,657 | 12/1994 | Irie . |
| 5,375,612 | 12/1994 | Cottenceau et al. . |
| 5,443,478 | 8/1995 | Purdy . |
| 5,490,859 | 2/1996 | Mische et al. . |
| 5,527,338 | 6/1996 | Purdy . |
| 5,531,788 | 7/1996 | Dibie et al. . |
| 5,693,067 | 12/1997 | Purdy . |
| 5,709,704 | 1/1998 | Nott et al. . |
| 5,720,764 | 2/1998 | Naderlinger . |
| 5,766,219 | 6/1998 | Horton . |
| 5,814,064 | 9/1998 | Daniel et al. ............................ 606/200 |
| 5,836,969 | 11/1998 | Kim et al. . |
| 5,868,708 | 2/1999 | Hart et al. . |
| 5,895,410 | 4/1999 | Forber et al. . |
| 5,911,734 | 6/1999 | Tsugita et al. .......................... 606/200 |
| 5,928,260 | 7/1999 | Chin et al. .............................. 606/200 |

OTHER PUBLICATIONS

Beathard, "Mechanical versus pharmacomechanical thrombolysis for the treatment of thrombosed dialysis access grafts," *Kidney Int.,* 45:1401–1406, 1994.

Beathard et al., "Mechanical thrombolysis for the treatment of thrombosed hemodialysis access grafts," *Radiology,* 200:711–716, 1996.

Ben–Menachem et al, "Hemorrhage associated with pelvic fractures: causes, diagnosis, and emergent management," *AJR,* 157:1005–1014, 1991.

(List continued on next page.)

*Primary Examiner*—Michael Buiz
*Assistant Examiner*—William Lewis
*Attorney, Agent, or Firm*—Fulbright & Jaworski

[57] ABSTRACT

A declotting method and apparatus. A declotting apparatus includes a catheter, a member positioned within the catheter, and a plurality of deformable members. The plurality of members bow and compress as the catheter slides relative to the member so that a site may be declotted. In another embodiment, a declotting apparatus includes a first and second catheter, a guidewire, a deformable jacket, and a liner. The deformable jacket expands and contracts as the first catheter slides relative to the second catheter so that a site may be declotted. The guidewire facilitates navigation, and the liner prevents material from entering the apparatus.

46 Claims, 6 Drawing Sheets

OTHER PUBLICATIONS

Bing et al, "Percutaneous ureteral occlusion with use of Gianturco coils and gelatin sponge, Part I. Swine model" *JVIR*, 3:313–317, 1992(a).

Bing et al, "Percutaneous ureteral occlusion with use of Gianturco coils and gelatin sponge, Part II. Clinical Experience," *JVIR*, 3:319–321, 1992(b).

Cambier et al, "Percutaneous closure of the small (<2.5 mm) patent ductus arteriosus using coil embolization," *Am. J. Cardiol.*, 69:815–816, 1992.

Castleman et al, "Biocompatibility of nitinol alloy as an implant material," *J. Biomed. Mater. Res.*, 10:695–731, 1976.

Dutton et al., "Pulmonary arteriovenous malformations: results of treatment with coil embolization in 53 patients," *AJR*, 165:1119–1125, 1995.

Feldman et al., "Vascular access morbidity in the US," *Kidney Int.*, 43:1091–1096, 1993.

Filcard International, "Instructions for use filcard temporary filter," 6 pages.

Furuse et al, "Hepatocellular carcinoma with portal vein tumor thrombus: embolization of arterioportal shunts," *Radiology*, 204:787–790, 1997.

Baxter Healthcare Corporation, Vascular Systems Division brochure, 3 pages.

Gianturco et al, "Mechanical device for arterial occlusion," *AJR*, 124:428–435, 1975.

Gray, "Percutaneous intervention for permanent hemodialysis access: A review," *JVIR*, 8:313–327, 1997.

Grifka et al, "Transcatheter patent ductus arteriosus closure in an infant using the Gianturco Grifka vascular occlusion device," *Am. J. Cardiol.*, 78:721–723, 1996.

Guglielmi et al, "Highflow, small–hole arteriovenous fistulas: treatment with electrodetachable coils," *AJNR*, 16:325–328, 1995.

Gunther et al., "Transrenal ureteral occlusion with a detachable balloon," *Radiology*, 142:521–523, 1982.

Hendrickx et al, "Long–term survival after embolization of potentially lethal bleeding malignant pelvic turnouts," *Br. J. Radiol.*, 68:1336–1343, 1995.

Hijazi and Geggel, "Results of anterograde transcatheter closure of patent ductus arteriosus using single or multiple Gianturco coils," *Am. J. Cardiol.*, 74:925–929, 1994.

Hijazi and Geggel, "Transcatheter closure of patent ductus arteriosus using coils," *Am. J. Cardiol.*, 79:1279–1280, 1997.

Hosking et al, "Transcatheter occlusion of the persistently patent ductus arteriosus," *Circulation*, 84:2313–2317, 1991.

Kinney et al., "Pulmonary emboli occurring with pulse–spray pharmacomechanical thrombolysis of clotted dialysis grafts with urokinase or heparinized saline," *JVIR Supplement*, 10(2) Part 2, p. 272–273, Feb., 1999.

Kónya et al, "Anchoring coil embolization in a high–flow arterial model," *JVIR*, 9:249–254, 1998.

Kónya et al., "Preliminary results with a new vascular occlusion device in an arterial model," *JVIR Supplement*, 9(1) Part 2, p. 213, Jan.–Feb., 1998.

Krichenko et al, "Angiographic classification of the isolated, persistently patent ductus arteriosus and implications for percutaneous catheter occlusion," *Am. J. Cardiol.*, 63:877–880, 1989.

Kumpe, "Fibrinolysis and angioplasty in the treatment of failed dialysis access sites," *JVIR Supplement*, 8(1) Part 2, p. 120–126, Jan.–Feb., 1997.

Latson, "Residual shunts after transcatheter closure of patent ductus arteriosus," *Circulation*, 84:2591–2593, 1991.

Lazzano et al., "Modified use of the Arrow–Trerotola percutaneous thrombolytic device for the treatment of thrombosed dialysis graft," *JVIR Supplement*, 10(2) Part 2, p. 233–234, Feb., 1999.

Liu and Stice, "Shape memory alloys and their applications," *J. Appl. Manufact. Sys.*, 3:65–72, 1990.

Lloyd et al, "Transcatheter occlusion of patent ductus arteriosus with Gianturco coils," *Circulation*, 88:1412–1420, 1993.

Magael et al, "A new device for transcatheter closure of patent ductus arteriosus: a feasibility study in dogs," *Invest. Radiol.*, 24:272–276, 1989.

Mailloux et al., "Survival estimates for 683 patients starting dialysis from 1970 through 1989: Identification of risk factors for survival," *Clin. Nephrol.*, 42:127–135, 1994.

Marks et al, "A mechanically detachable coil for the treatment of aneurysms and occlusion of blood vessels," *AJNR*, 15:821–827, 1994.

Masura et al, "Catheter closure of moderate to large sized patent ductus arteriosus using the new Amplatz duct occluder: immediate and short term results," *J. Am. Coll. Cardiol.*, 31:878–882, 1998.

Middlebrook et al., "Thrombosed hemodialysis grafts: percutaneous mechanical balloon declotting versus thrombolysis," *Radiology*, 196:73–77, 1995.

Nancarrow et al, "Stability of coil emboli: an in vitro study," *Cardiovasc. Intervent. Radiol.*, 10:226–229, 1987.

O'Halpin et al, "Therapeutic arterial embolization: report of five years' experience," *Clin. Radiol.*, 354:85–93, 1984.

Papanicoulau et al., "Percutaneous occlusion of ureteral leaks and fistulae using nondetachable balloons," *Urol. Radial.*, 7:28–31, 1985.

Pozza et al, "Transcatheter occlusion of patent ductus arteriosus using a newly developed self–expanding device: evaluation in a canine model," *Invest. Radiol.*, 30:104–109, 1995.

Punekar et al, "Post–surgical recurrent varicocele: efficacy of internal spermatic venography and steel–coil embolization," *Br. J. Urol.*, 77:12–128, 1996.

Rashkind et al, "Nonsurgical closure of patent ductus arteriosus: clinical application of the Rushkind PDA occluder system," *Circulation*, 75:583–592, 1987.

Reidy and Qureshi, "Interlocking detachable platinum coils, a controlled embolization device: early clinical experience," *Cardiovasc. Intervent. Radiol.*, 19:85–90, 1996.

Sagara et al, "Recanalization after coil embolotherapy of pulmonary arteriovenous malformations: study of long term outcome and mechanism for recanalization," *AJR*, 170:727–730, 1998.

Sanchez et al., "Urinary diversion by using a percutaneous ureteral occlusion device," *AJR*, 150; 1069–1070, 1988.

Schild et al, "Effectiveness of platinum wire microcoils for venous occlusion: a study on patients treated for venogenic impotence," *Cardiovasc. Intervent. Radiol.*, 17:170–172, 1994.

Schmitz–Rode et al, "Self–expandable spindle for transcatheter vascular occlusion: in vivo experiments," *Radiology*, 188:95–100, 1993.

Schwartz et al, "Effectiveness of transcatheter embolization in the control of hepatic vascular injuries," *JVIR*, 4:359–365, 1993.

Selby, Jr., "Interventional radiology of trauma," *Radiol. Clin. N. Am.*, 30:427–439, 1992.

Sharaffuddin et al, "Repositionable vascular occluder: experimental comparison with standard Gianturco coils," *JVIR*, 7:695–703, 1996.

Sharafuddin et al, "Experimental evaluation of a new self expanding patent ductus arteriosus occluder in a canine model," *JVIR*, 7:877–887, 1996.

Sommer et al, "Use of preformed nitinol snare to improve transcatheter coil delivery in occlusion of patent ductus arteriosus," *Am. J. Cardiol.*, 74:836–839, 1994.

Teitelbaum et al, "Microcatheter embolization of non–neurologic traumatic vascular lesions," *JVIR*, 4:149–154, 1993.

Tometzki et al., "Transcatheter occlusion of the patent ductus arteriosus with Cook detachable coils," *Heart*, 76:531–535, 1996.

"Transcatheter occlusion of persistent arterial duct." Report of the European Registry, Lancet, 340:1062–1066, 1992.

Trerotola et al., "Percutaneous use of the Fogarty adherent clot catheter," *JVIR*, 6:578–580, 1995.

Trerotola et al., "Thrombosed hemodialysis access grafts: percutaneous mechanical declotting without urokinase," *Radiology*, 191:721–726, 1994.

Trerotola, "Mechanical thrombolysis of hemodialysis grafts," *JVIR Supplement*, 8(1) Part 2, pp. 126–130, Jan.–Feb., 1997.

Uflacker et al., "Treatment of thrombosed dialysis access grafts: randomized trial of surgical thrombectomy versus mechanical thrombectomy with the amplatz device," *JVIR*, 7:185–192, 1996.

Uzun et al, "Transcatheter occlusion of the arterial duct with Cook detachable coils: early experience," *Heart*, 76:269–273, 1996.

Vedantham et al, "Uterine artery embolization: an underused method of controlling pelvic hemorrhage," *Am. J. Obstet. Gynecol.*, 176:938–948, 1997.

Vorwerk et al., "Hydrodynamic thrombectomy of hemodialysis fistulas: First clinical results," *JVIR*, 5:813–821, 1994.

Wallace et al, "Arterial occlusion of pelvic bone tumors," *Cancer*, 43: 322–328, 1979.

Wessel et al., "Outpatient closure of the patent ductus arteriosus," *Circulation*, 77:1068–1071, 1988.

White et al, "Pulmonary arteriovenous malformations: diagnosis and transcatheter embolotherapy," *JVIR*, 7:787–804, 1996.

Zubillaga et al, "Endovascular occlusion of intracranial aneurysms with electrically detachable coils: correlation of aneurysm neck size and treatment results," *AJNR*, 15:815–820, 1994.

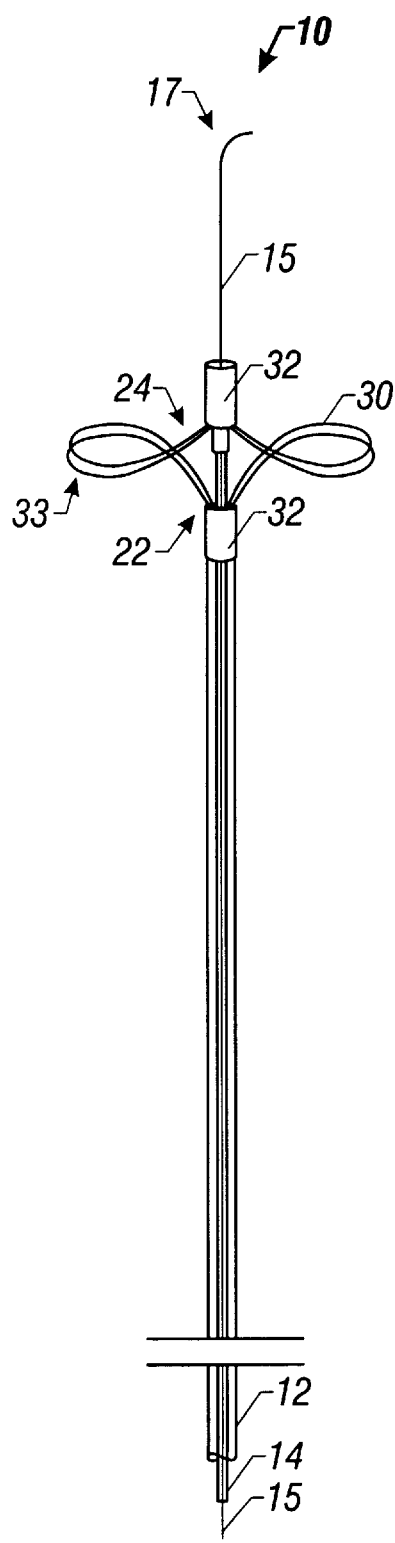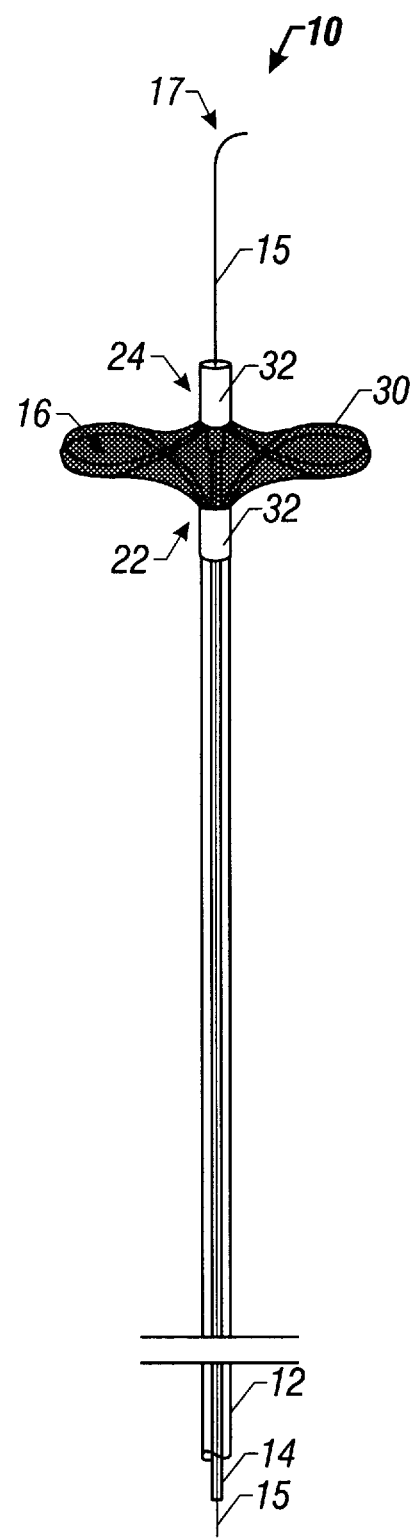
FIG. 4                    FIG. 5

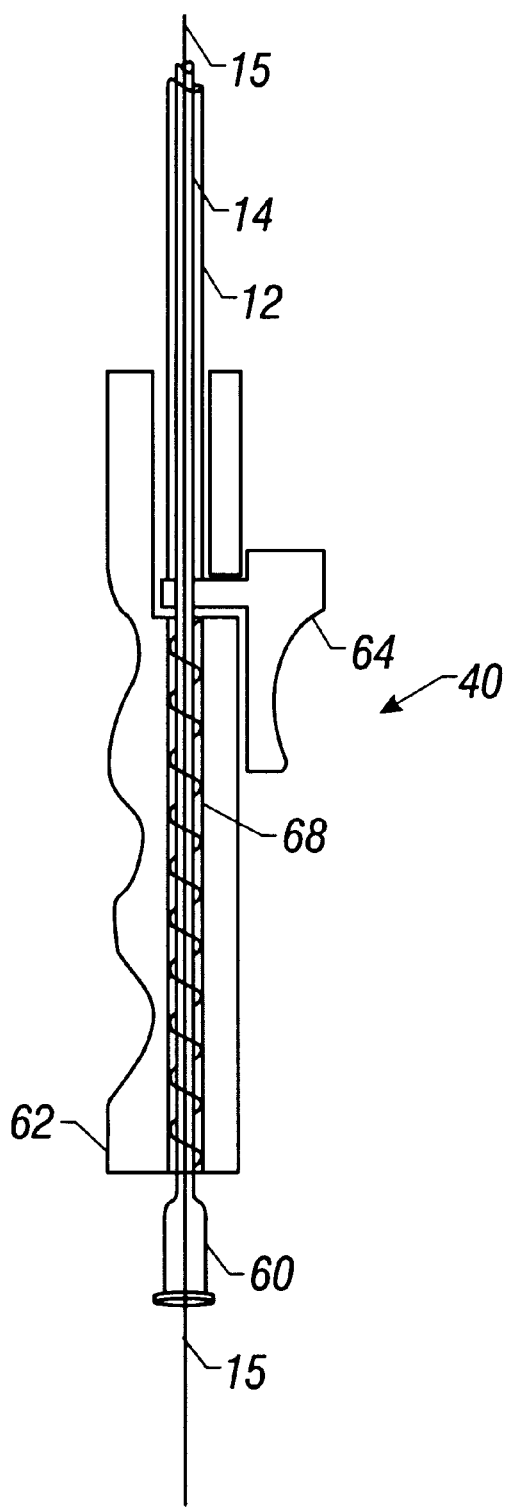 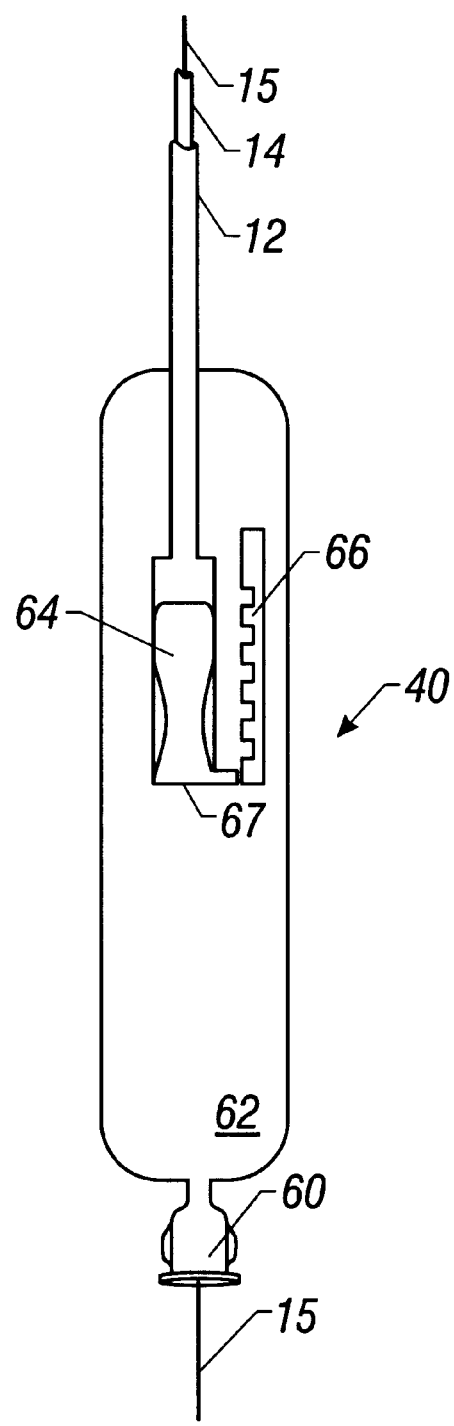
FIG. 9A  FIG. 9B

DECLOTTING METHOD AND APPARATUS

BACKGROUND OF THE INVENTION

1. Field of the Invention

The present invention relates generally to the field of interventional radiology. More particularly, it concerns a method and apparatus for reconstruction a flow path within a vascular conduit, and even more particularly, it concerns embolectomy and thrombectomy including treatment of thrombosed hemodialysis access grafts.

2. Description of Related Art

More than 129,000 patients are undergoing hemodialysis in the U.S. (Gray, 1997), and the leading cause for hospital admission is a problem related to life-sustaining access (Feldman, 1993). More than 80% of this patient population have a PTFE graft access which provides an average patency of 20 months after placement (Gray, 1997).

If one considers that the arterial and venous anatomy is typically sufficient to support three upper extremity grafts, a dialysis patient may expect an average 10 years (20 months times six grafts) of permanent access availability from upper extremities (Gray, 1997). Depending on the age when the kidneys fail, between 23 and 51% of patients will live at least 10 additional years after starting dialysis (Mailloux, 1994). If a renal transplant does not become available, many patients will need to resort to peritoneal dialysis or a less preferable hemodialysis access such as a lower extremity graft or a hemodialysis catheter. Some patients may even die because of lack of access. Therefore, efforts to maintain each available permanent hemodialysis access have become a matter of paramount importance.

There are at least three primary interventional radiology methods for percutaneous thrombolysis: urokinase infusion, pulse-spray pharmacomechanical thrombolysis with urokinase, and pure mechanical thrombolysis (Bethard, 1996; Trerotola, 1994; Beathard, 1994; Trerotola, 1997). The pharmacomechanical thrombolysis is often expensive because it may require a min. 350,000 and up to 1,200,000 U urokinase (approximately $100/100,000 U. The pulse-spray heparinized saline technique (Beathard, 1994), however, has proved as effective as the pulse-spray urokinase infusion in terms of long-term patency rates. The only statistically significant difference was that a without-urokinase-group took somewhat less time to complete. Recently, it has been found that the added urokinase reduced the rate of clinically asymptomatic pulmonary embolism (detected nuclear medicine perfusion scan), and the complications were more frequent with heparinized saline method (Kinney et al., 1999).

Several devices have been used to perform mechanical thrombolysis. A rotating nitinol basket-like fragmentation cage (Arrow-Trerotola Percutaneous Trombolytic Device) has been used by crossing 5-F sheaths within a graft and requires only a minute or two to restore flow. In a recent study, fifty-one consecutive patients were treated with the device. In all patients, the device was used to treat also the arterial plug in situ at the arterial anastomosis instead of using a Fogarty catheter to reposition the plug as indicated by the device's product labeling. Immediate technical patency was 100% with 6% arterial immobilization (vs 2% control). Adjunctive therapy with an Fogarty Adherent Clot catheter was needed in two procedures (4%). This modified method was found to be safe and effective when the device was used to eliminate the need for an Fogarty embolectomy catheter. (Modified use of the Arrow-Trerotola, 1999). The device costs cca. $500.

The Amplatz mechanical thrombectomy device (Clot Buster) (Microvena Co., has also been used successfully in dialysis grafts (Uflacker, 1996). This 8-F device consists of a gas-driven, high-speed (150,000 rpm) cam that pulverizes the clot. In a randomized series comparing surgical thrombectomy with the device, 89% success was achieved in the device group and 83% in the surgery group. Thirty-day patency was lower with the device (47%) than with surgery (77%). However, residual thrombus may occur with the device, and it cannot be used to treat the arterial plug. Recently the device has been made available also in a 6-French version. The cost of the disposable catheter is $550 and $900 (6-French/75-cm or 8-French/50-cm and 6-French/120-cm or 8-French/120-cm, respectively). The re-usable foot pedal assembly costs additionally. Because the device is not guidewire compatible, a 6-French ID or 8-French ID delivery sheath or a 8-French OD or 6-French OD guiding catheter should be used.

The Hydrolyser catheter (Cordis) uses the Venturi effect to achieve mechanical thrombolysis. The catheter is driven using a conventional angiographic injector. Although thrombectomy was successful in $15/16$ instances, five reclotted within 24 h. Secondary patency was 41% at 6 months (Vorwerk, 1994). One concern with this device, however, is the amount of blood aspirated during the procedure (50–150 mL) which could be problematic for these chronically anemic patients. This device is expected to cost $600.

The Cragg thrombolytic brush consisting of a 6-French brush catheter combines mechanical thrombolysis with urokinase to shorten procedure time and reduce urokinase dose. It is not a purely mechanical thrombolytic approach, but it takes advantage of many principles of mechanical thrombolysis. This 6-F device consists of a nylon brush that rotates at low speed (1,800 rpm.) driven by a single-use detachable motor drive. It is not guidewire compatible. It costs $595. Another similar design is the Castaneda Over-the Wire Brush (MTI) which is more preferred because of its guidewire compatibility. The brush itself is modified and allows for using the system forward and backward. The cost is also $595.

U.S. Pat. No. 4,921,484, incorporated herein by reference, discloses a device that uses a tubular mesh in a mesh balloon catheter device. Although this design has shown some utility, it does not offer guidewire compatibility. Thus, it may be necessary to use an additional device(s) to steer towards a desired place within a vessel.

Among simpler devices, the Fogarty Arterial Embolectomy Catheter (Baxter Scientific Products, McGaw Park, Ill.) ($45) has shown some utility in removing arterial clots. Although original Fogarty catheters were not guidewire compatible, guidewire compatible Fogarty balloons (Baxter) ($72) have recently been made available. Other over-the-wire alternatives include occlusion balloons ($110), and PTA balloons ($160–220) to macerate the clots. The basic technique for recanalization of hemodialysis access graft using these devices often consists of a cross-over catheterization requiring, unfortunately, multiple equipment. Specifically, two introducer sheaths and two balloon catheters are used. For dislodgment of an arterial plug or intragraft stenosis, the Fogarty Adherent Clot Catheter (Baxter) ($195) has been successfully used in some cases (Trerotola, 1995). Another similar alternative is the Fogarty Graft Thrombectomy Catheter (Baxter) ($325), which was designed to remove tough, mature thrombus from synthetic grafts. Except for the over-the wire Fogarty balloon, the other designs have no guidewire compatibility.

Despite many advantages, traditional mechanical thrombolytic devices often exhibit significant drawbacks. Some devices are large (8 F or more) and perform poorly in curved vessels, limiting their use in hemodialysis access. Residual adherent clot is a considerable problem with some of mechanical devices. Many devices do not remove the macerated clot and it may be embolized into the lungs. A great number of the available devices cannot be used over-the-wire.

The long term success rates of these methods are generally comparable to those of surgery which should be reserved for failures of percutaneous thrombolysis. Even successful intervention, however, does not eliminate the precipitating factors which cause intragraft thrombosis to occur. Recurrent thrombosis requires further interventions to be made on a regular basis until the dialysis access can be saved. On average, 0.5 to 0.8 episodes of access site thrombosis occur per patient-year of dialysis (Kumpe, 1997). Stenosis at or near the venous anastomosis is the most common cause of late access thrombosis. The endoluminal narrowing can be identified as the cause in cases up to 90% (Beathard, 1994).

Any problems pointed out in the foregoing are not intended to be exhaustive but rather are among many that tend to impair the effectiveness of previously known techniques. Other noteworthy problems may also exist; however, those presented above should be sufficient to demonstrate that previous techniques appearing in the art have not been altogether satisfactory, particularly in providing a rapid, effective, safe, easily performed, and minimally invasive outpatient procedure that will restore function to a thrombosed graft or vessel.

SUMMARY OF THE INVENTION

In one aspect, the invention is a declotting apparatus including a catheter, a member, and a plurality of deformable members. The member is positioned within the catheter and is slidable relative to the catheter. The plurality of deformable members form at least one loop and have a proximal portion and a distal portion. The proximal portion is coupled to the catheter at a proximal site, and the distal portion is coupled to the member at a distal site. The proximal site and the distal site are separated by a distance. The plurality of deformable members are configured to bow as the catheter slides to reduce the distance. The plurality of deformable members are configured to compress as the catheter slides to increase the distance.

In other aspects, the plurality of deformable members may form at least two loops. The plurality of deformable members may be programmed with thermal memory. The plurality of deformable members may be programmed with superelasticity. The plurality of deformable members may include nitinol wire. The plurality of deformable members may be elastically deformable. The declotting apparatus may also include a deformable jacket in operable relation to the plurality of deformable members. The jacket may be configured to cover at least a portion of the plurality of deformable members. The deformable jacket may be configured to expand as the plurality of deformable members bow, and the deformable jacket may be configured to contract as the plurality of deformable members compress. The deformable jacket may include braided stainless steel mesh. The declotting apparatus may also include a liner coupled to an inner surface of the deformable jacket. The liner may be configured to prevent material from entering an interior of the declotting apparatus. The declotting apparatus may also include a pair of clips coupled to the plurality of deformable members. The declotting apparatus may also include a sliding agent in operative relation to the catheter and the member and may be operable to slide the catheter relative to the member. The sliding agent may include a hand grip, a one-arm lever coupled to the hand grip and to the catheter, a luer adaptor coupled to the member, and a spring coupled to the hand grip and to the one-arm lever, with the spring extending therebetween. The sliding agent may include a grip body, a luer adaptor coupled to the grip body, a spring coupled to the grip body and configured to pull the catheter to compress the deformable members, a thumb button coupled to the spring and the catheter and configured to control the extent of compression of the deformable members, and; a ratchet mechanism in operative relation to the thumb button and configured to engage the thumb button to lock a position of the deformable members. The declotting apparatus may also include a lock in operative relation to the catheter and the member. The lock may be configured to fix the distance between the proximal site and the distal site. The declotting apparatus may also include an injection port and one or more injectors coupled to the catheter. The member may include a catheter. The declotting apparatus may also include a guidewire positioned within the catheter and extending through the distal site. The guidewire may be angled. The member may include a nitinol microtubing. The member may include a nitinol wire.

In another aspect, the invention is a declotting apparatus including a first catheter, a second catheter, a deformable jacket, a guidewire, and a liner. The first catheter defines a first lumen, and the second catheter defines a second lumen. The second catheter is positioned within the first lumen and is slidable relative to the first catheter. The deformable jacket has a proximal end and a distal end. The proximal end is coupled to the first catheter at a proximal site, and the distal end is coupled to the second catheter at a distal site. The guidewire is positioned within the second catheter and extends through the distal site. The liner is coupled to an inner surface of the deformable jacket and is configured to prevent material from entering an interior of the apparatus. The proximal site and the distal site are separated by a distance. The deformable jacket is configured to expand as the first catheter slides to reduce the distance. The deformable jacket is configured to contract as the first catheter slides to increase the distance.

In other aspects, the declotting apparatus may also include a plurality of deformable members coupled between the proximal site and the distal site. The plurality of deformable members may form at lease one loop. The plurality of deformable members may be programmed with thermal memory. The plurality of deformable members may be programmed with superelasticity. The plurality of deformable members may include nitinol wire. The declotting apparatus may also include a pair of clips coupled to the plurality of deformable members. The deformable jacket may include a braided stainless steel mesh. The declotting apparatus may also include a lock in operative relation to the first and second catheters and may be configured to fix the distance between the proximal site and the distal site. The declotting apparatus may also include a sliding agent in operative relation to the first and second catheters and operable to slide the first catheter relative to the second catheter. The declotting apparatus may also include an injection port and one or more injectors coupled to the first catheter. The second catheter may include a nitinol microtubing.

In another aspect, the invention is a method for declotting a site. A declotter including a catheter; a member positioned within the catheter; a plurality of deformable members forming at least one loop, the members having a proximal portion and a distal portion, the proximal portion being coupled to the catheter at a proximal site and the distal portion being coupled to the member at a distal site; the proximal site and the distal site being separated by a distance; and a deformable jacket in operable relation to the plurality of deformable members is provided. The plurality of deformable members are compressed by sliding the catheter relative to the member to increase the distance and to contract the deformable jacket. The declotter is positioned adjacent the site. The plurality of deformable members are bowed by sliding the catheter relative to the member to decrease the distance and to expand the deformable jacket to declot the site.

In other aspects, the method may also include locking the deformable jacket in a contracted state. The method may also include continuously modifying a diameter of the deformable jacket by sliding the catheter relative to the member. The declotter may also include an injection port and one or more injectors coupled to the catheter, and the method may also include injecting contrast through the declotter with the injection port. The site may be an thrombosed hemodialysis access graft site. The site may be a thrombosed intragraft site. The site may be a venous stenosis site.

In another aspect, the invention is a method for declotting a site. A declotter including a first catheter defining a first lumen; a second catheter defining a second lumen, the second catheter positioned within the first lumen; a guidewire positioned within the second catheter; a deformable jacket having a proximal end and distal end, the proximal end being coupled to the first catheter at a proximal site and the distal end being coupled to the second catheter at a distal site; wherein the proximal site and the distal site are separated by a distance; and a liner coupled to an inner surface of the deformable jacket is provided. The deformable jacket is contracted by sliding the first catheter relative to the second catheter to increase the distance. The declotter is maneuvered with the guidewire. The declotter is positioned adjacent the site. The deformable jacket is expanded by sliding the first catheter relative to the second catheter to decrease the distance to declot the site.

In other aspects, the method may also include preventing material from entering an interior of the declotter with the liner. The method may also include continuously modifying a diameter of the deformable jacket by sliding the first catheter relative to the second catheter. The site may be an thrombosed hemodialysis access graft site. The site may be a thrombosed intragraft site. The site may be a venous stenosis site.

Other features and advantages of the disclosed methods and apparatus will become apparent with reference to the following detailed description of embodiments thereof in connection with the accompanying drawings wherein like reference numerals have been applied to like elements, in which:

BRIEF DESCRIPTION OF THE DRAWINGS

FIG. 4 shows a declotting apparatus having looped deformable members according to one embodiment of the presently disclosed method and apparatus.

FIG. 5 shows a declotting apparatus having looped deformable members covered with a deformable jacket according to one embodiment of the presently disclosed method and apparatus.

FIG. 9A shows another sliding agent according to one embodiment of the presently disclosed method and apparatus.

FIG. 9B shows a top view of another sliding agent according to one embodiment of the presently disclosed method and apparatus.

DESCRIPTION OF ILLUSTRATIVE EMBODIMENTS

It will be appreciated that the presently disclosed methods and apparatus provide for certain significant advantages. For instance, the methods and apparatus allow for effective general declotting application, clot maceration, removal of an arterial plug, and the reduction or elimination of intragraft thrombosis(es). Because it may be flexible, the apparatus may be used with any suitable access shaft. A single apparatus may be used for cross-catheterization procedures so the number of devices needed to perform declotting may be advantageously reduced, which also reduces costs. Due to the continuously changeable diameter of the apparatus, optimal wall contact between the apparatus and a wall of, for instance, a graft may be achieved during manipulation. Its compact design, in one embodiment, provides controllable resistance and lets an operator better feel the apparatus during a given procedure. Due, in part, to its low profile, the apparatus does not require large access sheaths, although large access sheaths may be used if desired. Further, in one embodiment, the apparatus may be used with a suitable guidewire to facilitate maneuverability during a procedure. Its relatively simple design provides an inexpensive method and apparatus for declotting applications. In one embodiment, the apparatus advantageously allows for an injection port to inject, for example, contrast, heparin, or urokinase during a procedure.

Figure 1:
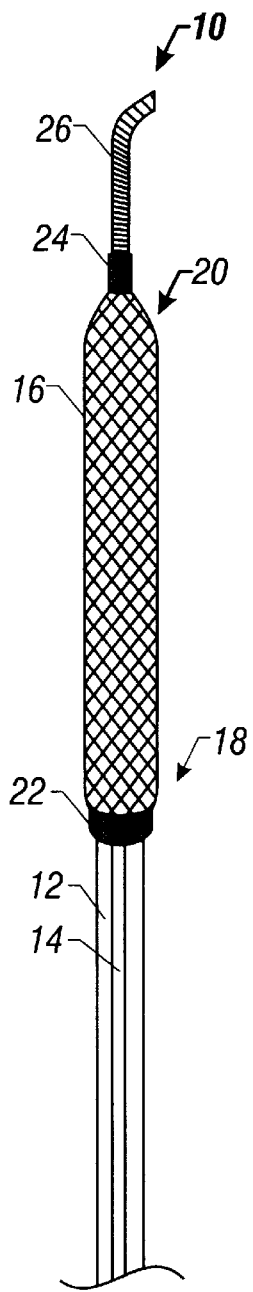
FIG. 1 shows a declotting apparatus in a contracted state according to one embodiment of the presently disclosed method and apparatus.

Turning first to FIG. 1, there is shown a declotting apparatus 10 according to one embodiment of the presently disclosed method and apparatus. Apparatus 10 includes a catheter 12, a member 14, and a deformable jacket 16. Jacket 16 has a proximal end 18 and a distal end 20. The proximal end is coupled to catheter 12 at proximal site 22. Distal end 20 is coupled to member 14 at distal site 24. As illustrated, proximal site 22 and distal site 24 may be separated by a distance. In operation, the distance between proximal site 22 and distal site 24 may be changed by sliding catheter 12 relative to member 14 so that deformable jacket 16 becomes expanded or contracted. It is to be understood that in other embodiments, member 14 may be moved relative to catheter 12 so as to achieve a similar effect upon deformable jacket 16. The expansion of deformable jacket 16 allows for the maceration of clots and for the declotting of a site, including, but not limited to a vascular stenosis, or a thrombosed hemodialysis polytetrafluroethylene (PTFE) graft site.

Figure 2:
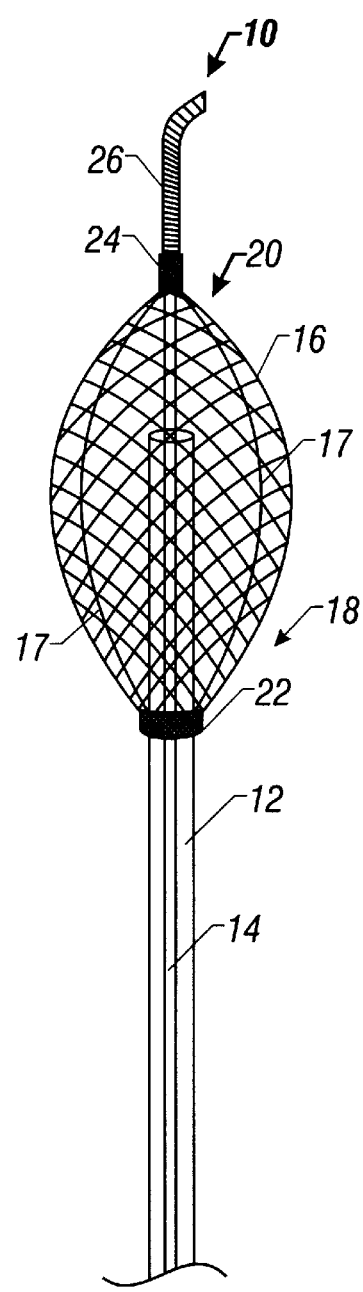
FIG. 2 shows a declotting apparatus in a partially expanded state in according to one embodiment of the presently disclosed method and apparatus.
Figure 3:
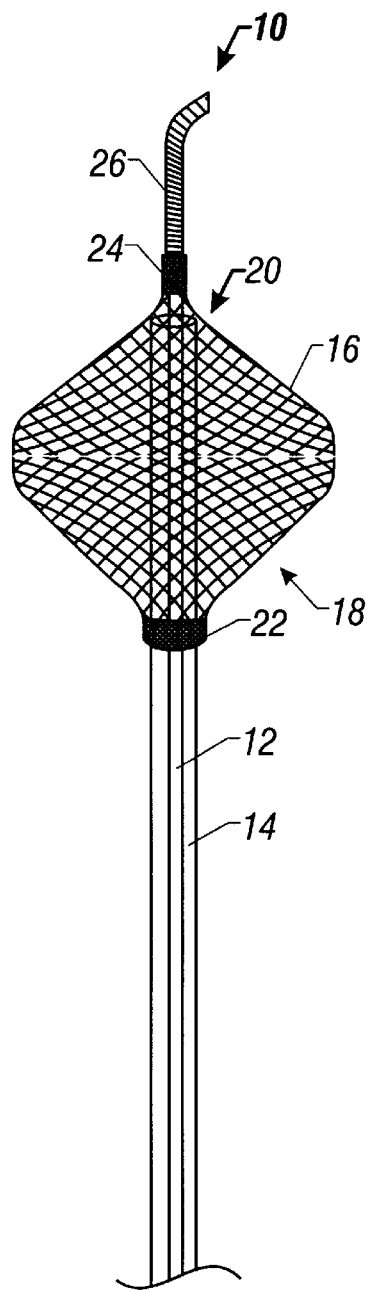
FIG. 3 shows a declotting apparatus in an expanded state according to one embodiment of the presently disclosed method and apparatus.

With reference to FIG. 1, FIG. 2 and FIG. 3, it may be seen how declotting apparatus 10 may be continuously expanded or contracted. With proximal end 18 being coupled to catheter 12 and distal end 20 being coupled to member 14, sliding catheter 12 relative to member 14 correspondingly changes the distance between proximal site 22 and distal site 24. That change in distance leads to a deformation of jacket 16 so that deformable jacket 16 expands or contracts. Declotting apparatus 10 may have a working profile that can be continuously changed and that can generate an expansile force for dilation. In FIG. 1, the distance between proximal site 22 and distal site 24 may be seen to be at or near a maximum value. In this configuration, declotting apparatus 10 may be said to be in a fully contracted state. In such a low-profile state, declotting apparatus 10 may be inserted through an appropriate access catheter or sheath and may be negotiated through, for instance, a hemodialysis graft.

In FIG. 2, it may be seen that the distance between proximal site 22 and distal site 24 is less than that shown in FIG. 1. In this state, it may be said that declotting apparatus 10 is in a semi-expanded state. As illustrated, as the distance between proximal site 22 and distal site 24 is reduced, deformable jacket 16 may be seen to expand, taking on a bowed or arcuate shape. Such an arcuate shape may allow for, for instance, the maceration of one or more clots. In FIG. 3, it may be seen that the distance between proximal site 22 and distal site 24 is less than that shown in FIG. 1 and FIG. 2. In such a configuration, it may be said that declotting apparatus 10 is in a fully expanded state. By fully expanded, it is meant that the distance between proximal site 22 and distal site 24 cannot be made shorter. As seen in FIG. 3, the distance may not be made shorter because catheter 12 may not slide more because distal site 24 blocks any further motion. In simpler terms, deformable jacket 16 cannot be further expanded because catheter 12 runs into distal site 24 so that further expansion of deformable jacket 16 may not occur. The degree to which deformable jacket 16 may be maximally expanded may be adjusted by setting the distance between the distal end of catheter 12 (i.e. the end closest to distal site 24) and distal site 24. In one embodiment, the distal end of catheter 12 may be about 25 mm from distal site 24.

Catheter 12 may be constructed of any suitable material of any suitable size, but in one embodiment, it may be constructed from Teflon, and it may have a diameter of about 4-F to 5-F. In one embodiment, the Teflon material ensures a smooth sliding movement relative to member 14. Catheter 12 may define a lumen in its interior to accommodate member 14. In one embodiment, member 14 may be a nitinol wire having a length of about 35 cm and a diameter of about 0.017–0.019-inches. However, with the benefit of the present disclosure, those having skill in the art will recognize that member 14 may be constructed of any suitable material and its size may vary according to need. In one embodiment, member 14 may itself be a catheter. In such an embodiment, member 14 may be constructed from any suitable material such as, but not limited to, Teflon, Nylon, or any suitable (firm but still flexible) plastic material. In one embodiment, member 14 may be a Teflon catheter have a diameter of about 2.5-French to about 3.5-French. In another embodiment, member 14 may be a superelastic Nitinol microtubing capable of accepting a guidewire of about 0.018-inches to about 0.0035-inches. In such an embodiment, the outer diameter of the Nitinol microtubing may be selected accordingly, from an OD of about 0.025-inches to about 0.040-inches. Those having skill in the art will recognize, however, that other relative sizes may be substituted therewith according to need.

As illustrated in FIG. 1, FIG. 2, FIG. 3 and FIG. 7, member 14 may extend beyond a distal site to define a guide 26. In one embodiment, guide 26 may be curved, angled, or otherwise may to conform to a suitable shape to facilitate, for example, the guidance of declotting apparatus 10 within an enclosure within a patient. Although here illustrated as being defined by member 14, it is contemplated that guide 26 may be distinct from member 14. In such an embodiment, guide 26 may be constructed from a material different than that of member 14. For example, guide 26 may be constructed from any suitable material including, but not limited to, stainless steel, nitinol, tungsten, or any combination of thereof. In one embodiment, guide 26 is composed of an inner core (stainless steel, nitinol) which is wrapped around a coil (stainless steel, tungsten). In embodiments where guide 26 is a distinct member, coupling to declotting apparatus 10 may be accomplished by any suitable manner known in the art. For example, guide 26 may be coupled to declotting apparatus 10 by tying, welding, gluing, clipping, fastening, crimping, or any combination thereof.

In one embodiment, proximal site 22 may be defined by any suitable coupling technique known in the art. For example, deformable jacket 16 may be coupled to catheter 12 at proximal site 22 by tying, crimping, fastening, gluing, welding, or any combination thereof. In embodiments where tying defines proximal site 22, the tying may be done with mono filament line such as Prolene 5-0, 6-0, 7-0 (polypropylene suture, Ethicon). Likewise, distal site 24 may be defined by any coupling technique well known in the art. For example, distal site 24 may be characterized by tying, crimping, fastening gluing, welding, or any combination thereof.

In one embodiment, deformable jacket 16 may be made from a braided mesh stainless steel. However, with the benefit of the present disclosure, those having skill in the art will recognize that many different suitable materials may be substituted therewith. For instance, in other embodiments, the deformable jacket 16 may be constructed from nitinol, or suitable plastic materials (e.g., nylon) In one embodiment, deformable jacket 16 may be meshed to facilitate the maceration of clots. In one embodiment, the relative rough outer surface of the braided stainless steel mesh makes the apparatus especially suitable for clot maceration and hemodialysis graft applications.

As deformable jacket 16 is maneuvered within a cavity, deformable jacket 16 may intercept portions of a clot and macerate that clot in the space between its meshed outer surface. The size and shape of deformable jacket 16 may vary widely according to need, but in one embodiment, deformable jacket 16 may extend to a diameter of about 6 mm and may form a fusiform shape when it is in a relaxed state. In one embodiment, the spacing of meshed material may be about 1-mm.

In one embodiment, deformable jacket 16 may include an inner liner 17 (FIG. 2). Such a liner may be useful to prevent any material, such as blood clots, from accumulating within the body of declotting apparatus 10. In one embodiment, inner liner 17 may be constructed from an ultra-thin (i.e.

about 0.02-mm) polyurethane cover, but it is to be understood that any other suitable material and thickness may be substituted therewith. Liner 17 may be coupled to deformable jacket 16 by any suitable manner known in the art, but in one embodiment coupling may be accomplished by gluing, or heating.

Turning now to FIG. 4, there is shown a declotting apparatus 10 that includes a catheter 12, a member 14, a plurality of deformable members 30, a proximal portion 22, a distal portion 24, a guidewire 15 having an angled portion 17, and a pair of clips 32. The operation of the embodiment illustrated in FIG. 4 is similar to that of the embodiments illustrated in FIG. 1, FIG. 2 and FIG. 3 in that the distance between proximal portion 22 and distal portion 24 may be modified so as to expand or contract the plurality of deformable members 30. More particularly, the distance may be modified to bow the plurality of deformable members 30 as the distance is reduced, and to compress the plurality of deformable members 30 as the distance is increased. The distance between proximal portion 22 and distal portion 24 may be changed by sliding catheter 12 relative to member 14 (or vice versa).

In one embodiment, catheter 12 may be a Teflon catheter having a diameter of about 4-F to 5-F, but it is to be understood that any other suitable material and size may be substituted therewith. Likewise, it will be understood by those having skill in the art any other suitable structure defining an interior lumen may be substituted for catheter 12. In one embodiment, member 14 may be a nitinol wire or other suitable structure. In the illustrated embodiment, member 14 is a catheter that defines an interior lumen. In one embodiment, member 14 may be a Teflon catheter having a diameter of about 2.5-French to about 3.5-French. Utilizing two Teflon catheters may provide for low friction sliding of catheter 12 relative to member 14.

In one embodiment, member 14 may accommodate guidewire 15. Guidewire 15 may be fixed relative to member 14 or it may slidable with relation to member 14. As illustrated, guidewire 15 may extend throughout declotting apparatus 10 and beyond distal portion 24 so that it may, for example, lead declotter 10 into an opening. In one embodiment, guidewire 15 may be constructed from nitinol, stainless steel, or any other suitable material. Although its diameter may vary widely according to application and the inner diameter of member 14, guidewire 15 may have a diameter of about 0.018-inches to about 0.035-inches. The end of guidewire 15, or any portion thereof, may be shaped according to need. With the benefit of this disclosure, those having skill in the art will recognize that any of commercially available guidewires having a suitable size may be used. As illustrated, guidewire 15 may include an angled tip shown by angled portion 17. In such an embodiment, guidewire 15 having angled tip may be used to effectively guide declotting apparatus within cavities such as vessels or grafts of a patient.

In the embodiment of FIG. 4, clips 32 may be configured to secure plurality of deformable members 30. Clips 32 may be coupled to the plurality of deformable members 30 by any means known in the art. In one embodiment, the coupling may include crimping. In other embodiments, welding, gluing, tying, threading, wrapping, or any combination thereof may be used. The size and materials making up clips 32 may vary, but in one embodiment the inventors made be made from stainless steel. Clips 32 may be coupled to catheter 12 and member 14 by any suitable technique known in the art. In one embodiment clip 32 may be coupled to catheter 12 by crimping. In other embodiments, welding, gluing, tying, threading, wrapping, or any combination thereof may be used. Likewise, clip 32 may be coupled to member 14 by crimping, welding, gluing, tying, threading, wrapping, or any combination thereof.

As may be seen in the embodiment of FIG. 4, plurality of deformable members 30 may take on a looped shape exhibited by arrow 33. In other words, at least one of the plurality of deformable members 30 may be shaped so that at least a portion of it may generally loop back on itself Such a configuration may advantageously allow for a more desirable shape upon being bowed as the distance between proximal portion 22 and distal portion 24 is decreased. The desirable shape may facilitate declotting. Although here shown as having a looped structure, those having skill in the art will recognize that any number of different shapes and configurations may be formed using the plurality of deformable members 30. For instance, deformable members 30 may be designed so that the inventors are arranged in arcuate conformation between pairs of clips 32. In the illustrated embodiment, four deformable members 30 are shown. However, it will be understood that more or fewer deformable members may be used. For instance, it is contemplated that two or more deformable members may be utilized to allow for effective expansion and contraction during operation so that declotting may be performed in accordance with the present disclosure. Although the size and material may vary widely, in one embodiment, deformable members 30 may be wires, and more particularly, nitinol wires having a diameter of about 0.006-inches to about 0.0011-inches.

In one embodiment, plurality of deformable members 30 may be elastically deformable. In such an embodiment, plurality of deformable members 30 may tend to recover their shape in the absence of any applied force (such as the force arising from the sliding of catheter 12 relative to member 14 of FIG. 4). In one embodiment, plurality of deformable members 30 may be programmed to exhibit thermal memory or superelasticity. Programming of superelasticity or thermal memory may be accomplished by any one of a number of techniques known in the art. In one embodiment utilizing nitinol wires having a diameter ranging anywhere from about 0.006 to 0.011 inches, programming may be achieved by first arranging deformable members 30 to form a desired arcuate shape. Having formed the desired shape, deformable members 30 may be secured into place by any suitable means. For instance, in one embodiment, deformable members 30 may be securedly wrapped around a ring of material, such as copper, so that deformable members 30 assume a desired arcuate shape. In another embodiment, a portion of deformable members 30 may be secured about an appropriately shaped material (such as a copper ring surrounding the body of the declotter) by being threaded through one or more holes formed in the material. In one embodiment, deformable members 30 may be threaded through two adjacent holes in a copper ring that surrounds the body of declotting apparatus 10. Being stretched so as to be threaded through the surrounding ring, deformable members 30 may form an arcuate shape. Being so secured in place, deformable members 30 may be exposed to heat for a certain period of time to complete the programming.

In one embodiment, heat exposure may be about 500 degrees Celsius, and the exposure time period may be about 5 to about 15 min to achieve superelasticity or about 60 to about 120 min to achieve thermal memory. With programming complete, deformable members 30 may easily be compressed or expanded at room temperature. With the benefit of the present disclosure, those of skill in the art will understand that different times and temperatures may be used to achieve programming of deformable members 30. Also, it will be understood that other methods may be used to accomplish superelasticity or thermal memory, and it will also be understood that such programming is optional— deformable members 30 made of appropriate elastic materials may be adapted to substantially recover an arcuate or other shape upon removal of a force naturally (i.e. without any need for heat or other types of programming).

Turning now to FIG. 5, there is shown a declotting apparatus 10 similar in design to the apparatus shown in FIG. 4. In the embodiment of FIG. 5, however, declotting 10 includes a deformable jacket 16 that covers plurality of deformable members 30. Although any suitable material may be used to construct deformable jacket 16, in one embodiment, deformable jacket 16 is constructed from a braided stainless steel mesh. In such an embodiment, small diameter wires (e.g., 0.001-inches to 0.004-inches) may be used to form the mesh. The mesh size may be about 1-mm or less. As was described with reference to FIG. 1, FIG. 2, FIG. 3, deformable jacket 16 may include a lining 17 (FIG. 2) that may prevent the accumulation of material, including clots, within the body of declotting apparatus 10.

In one embodiment, deformable jacket 16 may be made from a thin layer of a stretchable, preferably impermeable material (e.g., polyurethane and the like). In one embodiment, the thickness of such a layer may be about 0.02-mm to about 0.04 mm. The plurality of deformable members 30 may stretch the elastic material to form the desired work-profile of the device. Depending on the degree of expansion of deformable members 30 (that is, on the distance between clips 32) deformable jacket 16 may assume a shape of a flat disc (minimal distance between clips 32) or an elongated fusiform-shape (almost maximum distance between clips 32). Between the two extremes, any intermediate state may be used. In embodiments utilizing an impermeable material, separate lining 17 may be omitted, and material may still be prevented from entering the interior of the device.

Figure 6:
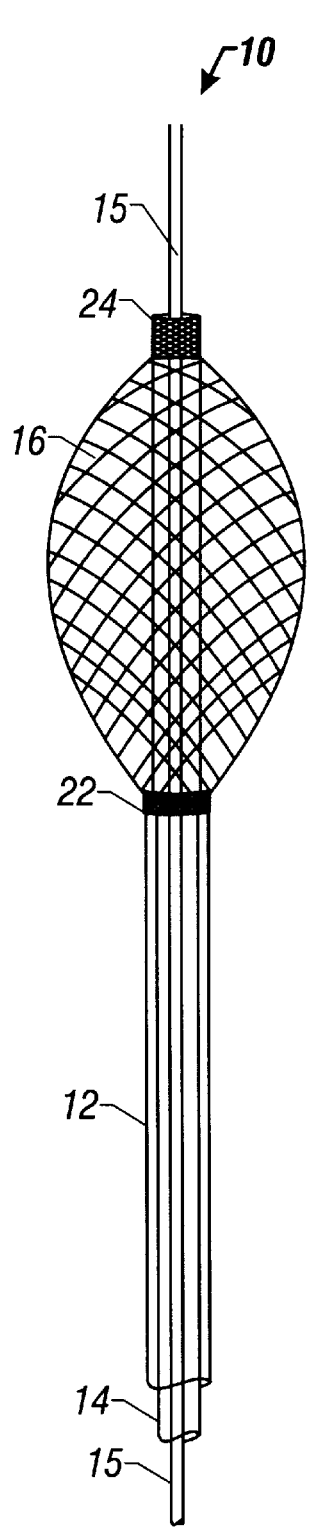
FIG. 6 shows a declotting apparatus including a guidewire according to one embodiment of the presently disclosed method and apparatus.

Turning now to FIG. 6, there is shown a declotting apparatus 10 including a guidewire 15 extending through distal site 24. This embodiment demonstrates that the size of guidewire 15 may be varied. In particular, it may be seen that the guidewire 15 of FIG. 6 is substantially larger than the guidewire illustrated in FIG. 4 and FIG. 5. As discussed previously, guidewire 15 may facilitate the maneuvering of declotting apparatus 10 and may be constructed from any suitable material known in the art including, but not limited to, nitinol and stainless steel. In particular, guidewire 15 may be any guidewire commercially available having a size suitable to fit within the working device. Those of skill in the art will recognize that apparatuses shown herein may be produced with or without guidewire compatibility. Accordingly, constructions of devices may vary somewhat from one another.

Figure 7:
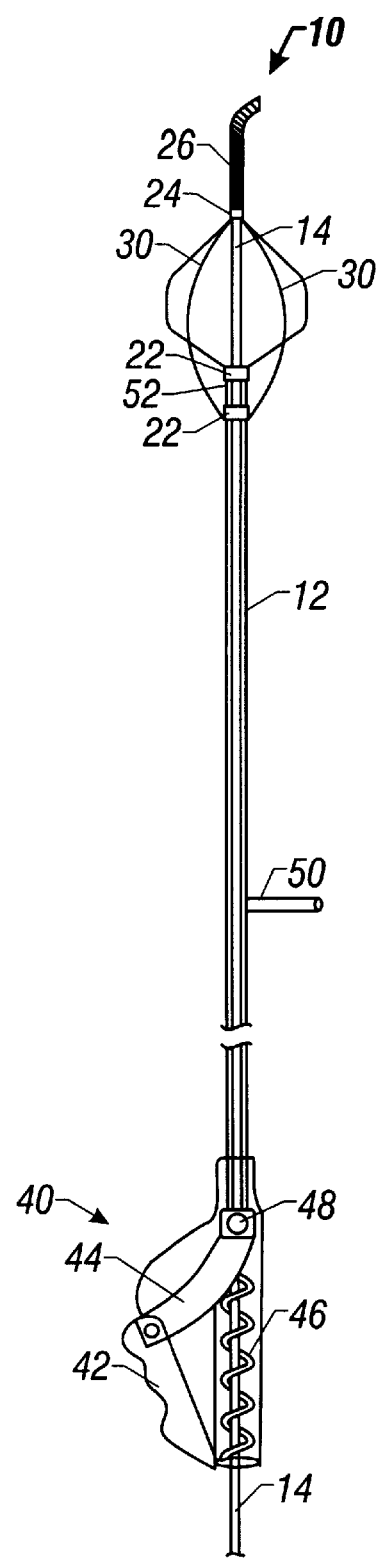
FIG. 7 shows a declotting apparatus including a sliding agent and injection port according to one embodiment of the presently disclosed method and apparatus.

Turning to FIG. 7 there is shown a declotting apparatus 10 that includes a catheter 12, a member 14, a guide 26, a proximal site 22, distal site 24, a plurality of deformable members 30, a sliding agent 40, an injection port 50, and an injector 52.

The embodiment of FIG. 7 is similar to the embodiments described previously, but in FIG. 7 it is demonstrated that a sliding agent 40 may be designed so as to slide catheter 12 relative to member 14. In the illustrated embodiment, sliding agent 40 includes hand grip 42, one-arm lever 44, spring 46, and attachment site 48. In operation, reducing the angle between one-arm lever 44 and hand grip 42 may move catheter 12 relative to member 14. More specifically, pressing one-arm lever 44 may move catheter 12 distally (i.e. towards distal site 24). Although here illustrated as utilizing a one-arm lever and hand grip, those having skill in the art will understand, with the benefit of the present disclosure, that sliding agent 40 may be configured in any number of suitable alternative manners. For instance, sliding agent 40 may include a single handle coupled to, for instance, catheter 12. Such a handle may allow for, for example, the direct sliding of catheter 12 relative to member 14. In one embodiment, one-arm lever 44 or any suitable alternative structure may be equipped with a lock mechanism that secures any possible position of catheter 12 relative to member 14 continuously without using any determined increments.

In one embodiment, spring 46 is a stainless steel spring and is connected to the proximal end of catheter 12, which may be a 4-F Teflon catheter. Spring 46 may pull the 4-F Teflon catheter back and, as a result of traction, the plurality of deformable members 30, which may be nitinol wires, may be stretched completely into a fully contracted state. The proximal end of the catheter/wire system may be equipped with a locking mechanism that keeps the deformable members 30 in a fully contracted state. After unlocking such a mechanism, continuous sliding movement between proximal site 22 and distal site 24 may be carried out by the one-armed lever mechanism illustrated, which may produce the movement of the 4-F Teflon catheter over second member 14, which may be a nitinol wire or another catheter, such as a Teflon catheter. Releasing lever 44, spring 46 may retract catheter 12 resulting in a small profile of the plurality of deformable members 30. It will be understood that although the above embodiment was described with relation to an embodiment utilizing deformable members 30 without a deformable jacket, the description applies equally well for all the other embodiments described herein.

In the illustrated embodiment of FIG. 7, injection port 50 may be configured to inject material into or adjacent declotting apparatus 10 during its manipulation within, for instance, a vessel. In the illustrated embodiment, injection port 50 includes a side arm coupled to the shaft of declotting apparatus 10. More particularly, in the embodiment of FIG. 7, injection port 50 may be coupled to catheter 12. In operation, a material may be introduced into injection port 50, and that material may travel within a lumen defined by catheter 12 and leading toward a plurality of deformable members 30 of declotting apparatus 10. The material introduced to injection port 50 may exit declotting apparatus 10 through a suitable injector. In the embodiment of FIG. 7, injector 52 may be configured to release material introduced via injection port 50 and traveling within catheter 12.

In FIG. 7, injector 52 may be an opening formed in, for instance, catheter 12. However, it will be understood that many different suitable designs may be substituted with the one shown for injector 52. For instance, one or more openings may be situated about catheter 12 or member 14 so that material introduced into injection port 50 or female Luer adapter (see element 60, FIG. 8) may be released from declotting apparatus 10 in one more different release patterns. In one embodiment, one to six side holes may be located close to the distal tip of catheter 12. In one embodiment, injector 52 may be configured to spray a material adjacent declotting apparatus 10. Injection port 50 and injector 52 may be utilized, in one embodiment, to inject contrast near declotting apparatus 10. In other embodiments, injection port 50 and injector 52 may be utilized to inject heparin and/or urokinase solution directly into a target area so that thrombolysis may be promoted. With the benefit of the present disclosure those having skill in the art will recognize that any number of other materials may be injected from declotting apparatus 10 to perform any number of varying applications.

Figure 8:
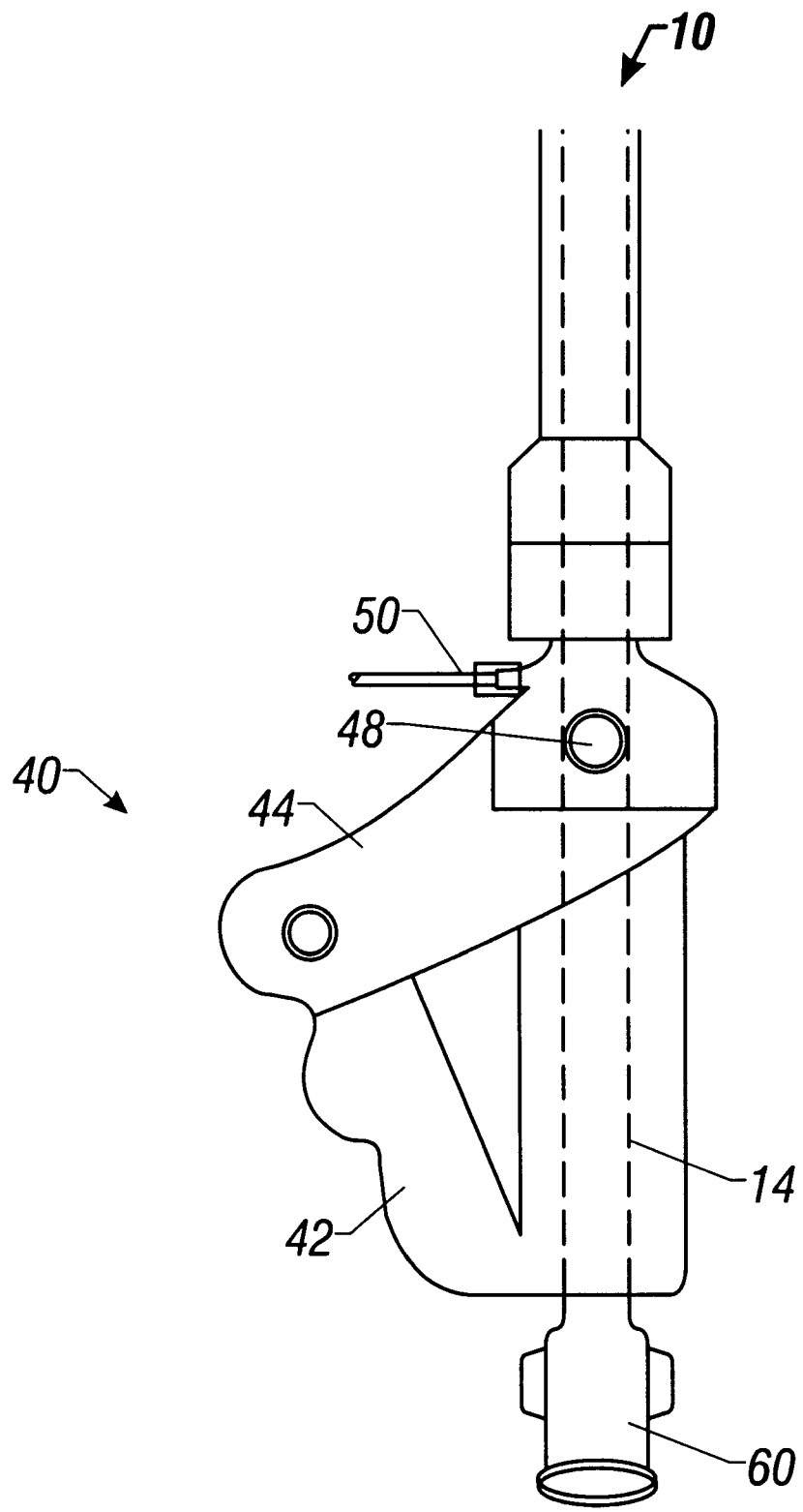
FIG. 8 shows a sliding agent according to one embodiment of the presently disclosed method and apparatus.

Turning to FIG. 8, there is shown another embodiment utilizing an injection port 50. There, it may be seen that a female Luer adapter 60 may be coupled to member 14 (provided that member 14 defines a lumen). In this embodiment, Luer attachment 60 may serve at least two goals: it may accept a guidewire, and it allows some fluid to be injected through a lumen of member 14. In one embodiment, member 14 may be equipped with multiple side holes between proximal site 22 and distal site 24 (see, e.g., FIG. 7) provided that deformable jacket 16 is not equipped with lining 17. If lining 17 is coupled to deformable jacket 16 or deformable members 30, side holes may be created outside the distal portion of 14 covered by such a lining 17. For example, holes may be positioned, in one embodiment, between distal site 24 and guide 26 or close to the distal tip of catheter 12. The Luer attachment site 60 may enable one, in one embodiment, to attach a check-flow adapter with a check-flow valve and a side arm; using this assembly, some fluid (contrast, heparin, urookinase, or the like) may be injected even if a guidewire is positioned within a lumen defined by member 14.

In the embodiment of FIG. 7, it may be seen that there may be one more than one proximal sites 22. Such an embodiment demonstrates that different deformable members 30 may be coupled to catheter 12 at different locations along catheter 12. Being coupled at different locations, plurality of deformable members 30 may be made to define different shapes. For instance, in the illustrated embodiments, it may be seen that deformable members 30 may define a shape having a wider upper portion and a thinner lower portion. More specifically, in the illustrated embodiment, the deformable member 30 that is coupled at a higher location along catheter 12 assumes a wider shape than deformable member 30 that have a lower proximal site. Although not so illustrated, it is contemplated that coupling sites along member 14 may be spaced so that a desired shape of declotting apparatus 10 may be achieved. For instance, each of the plurality of deformable members 30 may be coupled to member 14 at slightly different distal sites 24 so that a unique shape may be formed.

Turning to FIG. 9A and FIG. 9B, there are shown other embodiments for a sliding agent 40. In these embodiment, spring 68 may be configured to pull the proximal end of catheter 12 to stretch/elongate the working profile of declotter 10. The declotter may be expanded, or "activated", by pushing thumb-button 64 coupled to grip body 62 and to the outer surface of catheter 12 distally. As a result, the working profile of declotter 10 may increase in diameter. In one embodiment, thumb-button 64 may be fixed at certain points by ratchet mechanism 66. In particular, portion 67 may engage ratchet mechanism 66 so as to lock thumb button 64, and consequently the diameter of declotter 10, in place. In one embodiment, such a locking may be accomplished by pushing thumb-button 64 distally and then laterally to fix it in position within ratchet mechanism 66. Using such an embodiment, one may achieve a series of controllable, different sizes of the working profile of declotter 10. More specifically, deformable jacket 16, of for instance, FIG. 1, or plurality of deformable members 30 of, for instance, FIG. 4 may be fixed in place so that a desirable diameter may be easily maintained.

Figure 10:
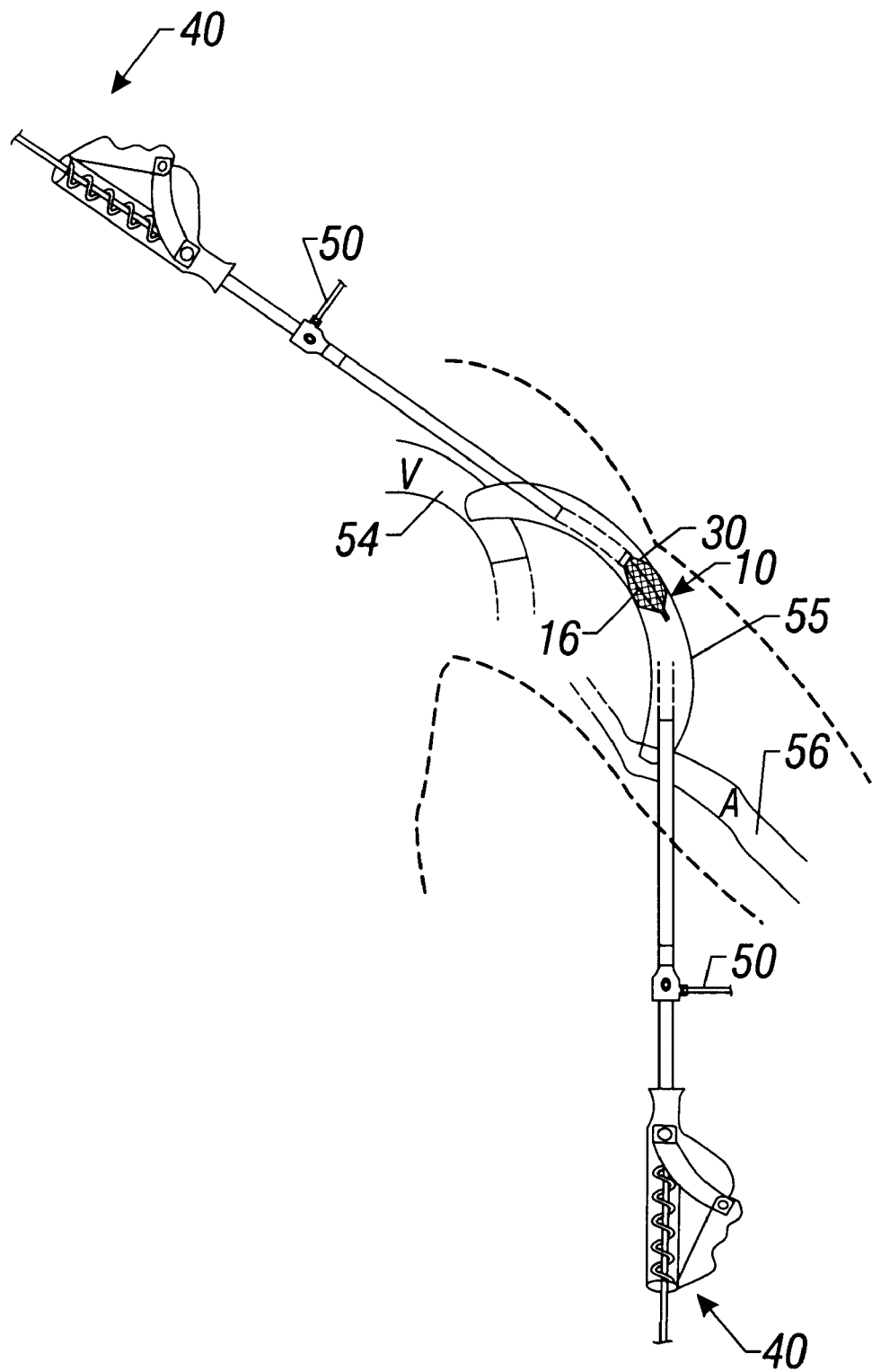
FIG. 10 shows a declotting apparatus being used to recanalize a hemodialysis access graft sight according to one embodiment of the presently disclosed method and apparatus.

Turning to FIG. 10, there is shown a declotting apparatus 10 being used for the recanalization of a hemodialysis PTFE graft 55. As illustrated, declotting apparatus 10 may be utilized as a recanalization of both venous and arterial limbs of the hemodialysis graft 55. Treatment with declotting apparatus 10 may be performed subsequent to balloon angioplasty of all possible stenoses. In one embodiment, recanalization of the venous limb may be achieved by using declotting apparatus 10 to dislodge one or more soft clots of the venous limb of graft 55. Declotting apparatus 10 may be moved back and forth while continuously changing the diameter of a deformable jacket or of a plurality of deformable members as described herein. Clots may be aspirated (Bethard, 1996) or pushed toward central veins (Trerotola, 1994; Middlebrook, 1995). By using declotting apparatus 10 with a changing diameter, intragraft stenoses may be macerated and dislodged.

In case of intragraft stenosis, one may dilate the graft itself to macerate clots further (Beathard, 1996). In these cases, the declotting apparatus 10 offers a combined approach: using the apparatus with a changing diameter, taking advantage of the strong and continuously controllable wall contact between the device and the graft wall, plus utilizing the dilation capacity of the device, the intragraft stenosis(es) can be macerated and dislodged. After balloon dilation, thrombi may remain in place partially compressed to the wall of the graft and may induce a new thrombotic process. For removal of the arterial plug, the declotting apparatus 10 may be passed across the arterial anastomosis in its completely stretched profile (i.e. in a contracted state). The deformable jacket or plurality of deformable members may then be expanded so that the apparatus assumes the diameter of the parent artery and is gently pulled back to the tip of the insertion sheath located in the venous limb of the graft. In this case, the device may be used in a manner similar to a Fogarty embolectomy catheter.

In one embodiment, treatment of a thrombosed hemodialysis access graft may include two parts: restore the flow in the venous side eliminating the stenosis(es) and restore the flow within the graft. The stenosis at the venous anastomosis (together with possible more proximal stenoses located in the central veins) may be treated first with angioplasty. To eliminate the venous stenosis the embodiment that uses a braided stainless steel mesh as deformable jacket 16 may be used. In this application, the device may be used to exert lateral forces to the lesion, eliminating the need for using a dilatation balloon catheter for this purpose. The second step may be clot maceration in the graft (especially in the venous limb), as well as the removal of intragraft thromboses and the arterial plug. In the embodiments described herein, it will be understood that the same declotting apparatus 10 may be utilized for recanalization of both the venous and the arterial limbs of the hemodialysis graft. Additionally, it will be understood that an access sheath may be used for insertion in all of these embodiments. In particular, declotting apparatus 10 may take on a contracted state (and, as described in relation to FIG. 7, may be locked in such a state) so that the apparatus may be inserted into an access sheath or guide, such as a guiding catheter.

Although FIG. 10 illustrates the recanalization of an access graft 55, those having skill in the art will understand that the applications for declotting apparatus 10 are indeed vast. For example, the design may also be used in all applications where other designs, including, but not limited to, designs mentioned in the Description of Related Art section of this disclosure. For instance, one possible application may be to remove thrombus/embolus from native arteries or from PTFE or other synthetic arterial grafts (replacing the widely used Fogarty Embolectomy Catheter, Fogarty Adherent Clot Catheter or Fogarty Graft Thrombectomy Catheter (all from Baxter). Clots developing in synthetic graft materials may be highly organized, more mature, and adherent. Their removal may require stronger devices because balloons tend to rupture. Utilizing the radial force exerted by the device as disclosed herein, the presently described apparatus may be used instead of a dilatation balloon catheter to treat short stenoses within the vasculature. The continuously changeable working profile of the disclosed apparatus along with its expansile force (in particular, embodiments utilizing a braided mesh design) may enable one to recanalize long segments of diseased arteries or veins.

In general, the disclosed method and apparatus may be used for, but is not limited to declotting a thrombosed hemodialysis a-v graft, clot maceration (instead of occlusion-type balloon catheters or angioplasty), removal of arterial plug (instead of a Fogarty balloon catheter or a Fogarty Adherent Clot Catheter), elimination of intragraft thrombosis(es) (instead of angioplasty balloon catheters or Fogarty Adherent Clot Catheters), and angioplasty of the venous stenosis (instead of angioplasty balloon catheters).

For angioplasty of the venous stenosis, one embodiment for declotting may include, but is not limited to the following steps. The stenosis at the venous anastomosis may be treated first using a presently disclosed declotter 10 in a manner similar to an angioplasty device. Clot maceration may be done using the device in a manner similar to an occlusion-balloon/or PTA balloon. Elimination of intragraft thromboses may be accomplished using the device in a manner similar to an angioplasty device. Removal of the arterial plug may be accomplished using the device in a manner similar to a Fogarty embolectomy balloon or device.

In one embodiment, a declotter 10 may be produced in a length (e.g., about 60 cm to about 100 cm) that allows for using the design for embolectomy/thrombectomy/angioplasty in locations other than the a-v graft. In one embodiment, emboli may be removed from the peripheral arteries or pulmonary arteries. During such a procedure, the declotter may be advanced over a guidewire behind the embolus, then the working profile may be activated. The profile, which in one embodiment may include a braided mesh deformable jacket, may then be pulled back and out from the body together with the entrapped embolus.

A further application may be to use a disclosed device for recanalization of lengthy arterial or venous stenoses or occlusions. In such an application, a device may travel over a guidewire that has been advanced trough the seriously stenosed and/or completely occluded segment of the vessel. The recanalization may consist of a series of repeated movements such as (a) working profile activation, (b) profile deactivation (relaxation), profile advancement, profile activation, profile relaxation, and so forth, until the afflicted lumen becomes patent.

In such an application, the device may be used over a guidewire that has been negotiated through the stenosed and/or occluded segment of the vessel. The device may be moved distally in a determined length (determined, for instance, by the length of deformable jacket 16) guided by the guidewire. The work-profile of the device may be "activated". The compressible material (such as atherosclerotic mass and/or thrombus) may be pressed onto the internal layer of the vessel and/or between the layers of the vessel. This mechanism is well known in the art as the technique of angioplasty. The treated segment's lumen may increase in size. The device may then be moved distally in another determined length and the procedure may be repeated. After a series of dilations, the lumen of the afflicted vessel may be be rendered widely patent. The procedure may be repeated during withrawal of the device all along proximally. The procedure may be facilitated by injecting contrast, heparin, or urokinase for quickness and safety. This procedure (recanalization) may be followed by placement of a stent or stents to maintain the achieved patency.

While the present disclosure may be adaptable to various modifications and alternative forms, specific embodiments have been shown by way of example and described herein. However, it should be understood that the present disclosure is not intended to be limited to the particular forms disclosed. Rather, it is to cover all modifications, equivalents, and alternatives falling within the spirit and scope of the disclosure as defined by the appended claims. For instance, the disclosed apparatus may utilize different orientations of components, sizes of components, or materials according to needs. Moreover, the different aspects of the disclosed methods and apparatuses may be utilized in various combinations and/or independently. Thus the invention is not limited to only those combinations shown herein, but rather may include other combinations. In other words, those of skill in the art should, in light of the present disclosure, appreciate that many changes can be made in the specific embodiments that are disclosed and still obtain a like or similar result without departing from the spirit and scope of the invention.

REFERENCES

The following references, to the extent that they provide exemplary procedural or other details supplementary to those set forth herein, are specifically incorporated herein by reference.

U.S. Pat. No. 4,921,484

Beathard, "Mechanical versus pharmacomechanical thrombolysis for the treatment of thrombosed dialysis access grafts," *Kidney Int.,* 45:1401–1406, 1994.

Bethard, Welch, Maidment, "Mechanical thrombolysis for the treatment of thrombosed hemodialysis access grafts," *Radiology,* 200:711–716, 1996.

Feldman, Held, Hutchinson et al., "Vascular access morbidity in the US," *Kidney Int.,* 43:1091–1096, 1993.

Gray, "Percutaneous intervention for permanent hemodialysis access: A review," *JVIR,* 8:313–327, 1997.

Kinney, Valji, Rose, Yeung, Oglevie, Roberts et al., "Pulmonary emboli occurring with pulse-spray pharmacomechanical thrombolysis of clotted dialysis grafts with urokinase or heparinized saline," Abstract No. 169, p 272, 24th Annual Scientific Meeting of SCVIR, Orlando, Fla., Mar. 20–25, 1999.

Kumpe, "Fibrinolysis and angioplasty in the treatment of failed dialysis access sites," In: *JVIR Supplement,* Scientific Program of SCVIR 22nd Annual Scientific Meeting, Washington, D.C., pp 120–126, Mar. 8–13, 1997.

Mailloux, Bellucci, Napolitano, Mossey, Wilkes, Bluestone, "Survival estimates for 683 patients starting dialysis from 1970 through 1989: Identification of risk factors for survival," *Clin. Nephrol.,* 42:1127–135, 1994.

Middlebrook, Amygdalos, Soulen, Haskal, Shlansky-Goldberg, Cope, Pentecost, "Thrombosed hemodialysis grafts: percutaneous mechanical balloon declotting versus thrombolysis," *Radiology,* 196:73–77, 1995.

"Modified use of the Arrow-Trerotola percutaneous thrombolytic device for t treatment of thrombosed dialysis graft," Abstract No. 71, p 233, 24th Annual Scientific Meeting of SCVIR, Orlando, Fla., Mar. 20–25, 1999.

Trerotola, "Mechanical thrombolysis of hemodialysis grafts," In: *JVIR Supplement,* Scientific Program of SCVIR 22nd Annual Scientific Meeting, Washington, D.C., pp 126–130, Mar. 8–13, 1997.

Trerotola, Harris, Snidow, Johnson, "Technical note: percutanous use of the Fogarty adherent clot catheter," *JVIR,* 6:578–580, 1995.

Trerotola, Lund, Scheel, Savader, Venbrux, Osterman, "Thrombosed hemodialysis access grafts: percutanenous mechanical declotting without urokinase," *Radiology,* 191:721–726, 1994.

Uflacker, Rajagopalan, Vujic, Stutley, "Treatment of thrombosed dialysis access grafts: Randomized trial of surgical thrombectomy versus mechanical thrombectomy with the Amplatz device," *JVIR,* 7:185–192, 1996.

Vorwerk, Sohn, Schurmann, Hoogeveen, Gladziwa, Guenther, "Hydrodynamic thrombectomy of hemodialysis fistulas: First clinical results," *JVIR,* 5:813–821, 1994.

What is claimed is:

1. A declotting apparatus comprising:
   a catheter;
   a member positioned within said catheter, said member slidable relative to said catheter;
   a plurality of deformable members forming at least one loop, said members having a proximal portion and a distal portion, said proximal portion being coupled to said catheter at a proximal site and said distal portion being coupled to said member at a distal site;
   wherein said proximal site and said distal site are separated by a distance;
   wherein said plurality of deformable members are configured to bow as said catheter slides to reduce said distance; and
   wherein said plurality of deformable members are configured to compress as said catheter slides to increase said distance.

2. The apparatus of claim 1, wherein said plurality of deformable members form at least two loops.

3. The apparatus of claim 1, wherein said plurality of deformable members are programmed with thermal memory.

4. The apparatus of claim 1, wherein said plurality of deformable members are programmed with superelasticity.

5. The apparatus of claim 1, wherein said plurality of deformable members comprise nitinol wire.

6. The apparatus of claim 1, wherein said plurality of deformable members are elastically deformable.

7. The apparatus of claim 1, further comprising a deformable jacket in operative relation to said plurality of deformable members and configured to cover at least a portion of said plurality of deformable members.

8. The apparatus of claim 7, wherein said deformable jacket is configured to expand as said plurality of deformable members bow and wherein said deformable jacket is configured to contract as said plurality of deformable members compress.

9. The apparatus of claim 7, wherein said deformable jacket comprises braided stainless steel mesh.

10. The apparatus of claim 7, further comprising a liner coupled to an inner surface of said deformable jacket and configured to prevent material from entering an interior of said apparatus.

11. The apparatus of claim 1, further comprising a pair of clips coupled to said plurality of deformable members.

12. The apparatus of claim 1, further comprising a sliding agent in operative relation to said catheter and said member and operable to slide said catheter relative to said member.

13. The apparatus of claim 12, wherein said sliding agent comprises:
   a hand grip;
   a one-arm lever coupled to said hand grip and to said catheter;
   a luer adaptor coupled to said member; and
   a spring coupled to said hand grip and to said one-arm lever, said spring extending therebetween.

14. The apparatus of claim 12, wherein said sliding agent comprises:
   a grip body;
   a luer adaptor coupled to said grip body;
   a spring coupled to said grip body and configured to pull said catheter to compress said deformable members;
   a thumb button coupled to said spring and said catheter and configured to control the extent of compression of said deformable members; and
   a ratchet mechanism in operative relation to said thumb button and configured to engage said thumb button to lock a position of said deformable members.

15. The apparatus of claim 1, further comprising a lock in operative relation to said catheter and said member and configured to fix the distance between said proximal site and said distal site.

16. The apparatus of claim 1, further comprising an injection port and one or more injectors coupled to said catheter.

17. The apparatus of claim 1, wherein said member comprises a catheter.

18. The apparatus of claim 17, further comprising a guidewire positioned within said catheter and extending through said distal site.

19. The apparatus of claim 18, wherein said guidewire is angled.

20. The apparatus of claim 1, wherein said member comprises a nitinol microtubing.

21. The apparatus of claim 1, wherein said member comprises a nitinol wire.

22. A declotting apparatus comprising:
   a first catheter defining a first lumen;
   a second catheter defining a second lumen, said second catheter positioned within said first lumen, said second catheter slidable relative to said first catheter;
   a deformable jacket having a proximal end and distal end, said proximal end being coupled to said first catheter at a proximal site and said distal end being coupled to said second catheter at a distal site;
   a guidewire positioned within said second catheter and extending through said distal site;
   a liner coupled to an inner surface of said deformable jacket and configured to prevent material from entering an interior of said apparatus;
   wherein said proximal site and said distal site are separated by a distance;
   wherein said deformable jacket is configured to expand as said first catheter slides to reduce said distance; and
   wherein said deformable jacket is configured to contract as said first catheter slides to increase said distance.

23. The apparatus of claim 22, further comprising a plurality of deformable members coupled between said proximal site and said distal site.

24. The apparatus of claim 23, wherein said plurality of deformable members form at lease one loop.

25. The apparatus of claim 23, wherein said plurality of deformable members are programmed with thermal memory.

26. The apparatus of claim 23, wherein said plurality of deformable members are programmed with superelasticity.

27. The apparatus of claim 23, wherein said plurality of deformable members comprise nitinol wire.

28. The apparatus of claim 23, further comprising a pair of clips coupled to said plurality of deformable members.

29. The apparatus of claim 22, wherein said deformable jacket comprises braided stainless steel mesh.

30. The apparatus of claim 22, further comprising a lock in operative relation to said first and second catheters and configured to fix the distance between said proximal site and said distal site.

31. The apparatus of claim 22, further comprising a sliding agent in operative relation to said first and second catheters and operable to slide said first catheter relative to said second catheter.

32. The apparatus of claim 22, further comprising an injection port and one or more injectors coupled to said first catheter.

33. The apparatus of claim 22, wherein said second catheter comprises a nitinol microtubing.

34. A method for declotting a site, comprising:
providing a declotter including: a catheter; a member positioned within said catheter; a plurality of deformable members forming at least one loop, said members having a proximal portion and a distal portion, said proximal portion being coupled to said catheter at a proximal site and said distal portion being coupled to said member at a distal site; said proximal site and said distal site being separated by a distance; and a deformable jacket in operable relation to said plurality of deformable members;
compressing said plurality of deformable members by sliding said catheter relative to said member to increase said distance and to contract said deformable jacket;
positioning said declotter adjacent said site; and
bowing said plurality of deformable members by sliding said catheter relative to said member to decrease said distance and to expand said deformable jacket to declot said site.

35. The method of claim 34, further comprising locking said deformable jacket in a contracted state.

36. The method of claim 34, further comprising continuously modifying a diameter of said deformable jacket by sliding said catheter relative to said member.

37. The method of claim 34, wherein said declotter further comprises an injection port and one or more injectors coupled to said catheter, and wherein said method further comprises injecting contrast through said declotter with said injection port.

38. The method of claim 34, wherein said site is an thrombosed hemodialysis access graft site.

39. The method of claim 34, wherein said site is a thrombosed intragraft site.

40. The method of claim 34, wherein said site is a venous stenosis site.

41. A method for declotting a site, comprising:
providing a declotter including: a first catheter defining a first lumen; a second catheter defining a second lumen, said second catheter positioned within said first lumen; a guidewire positioned within said second catheter; a deformable jacket having a proximal end and distal end, said proximal end being coupled to said first catheter at a proximal site and said distal end being coupled to said second catheter at a distal site; wherein said proximal site and said distal site are separated by a distance; and a liner coupled to an inner surface of said deformable jacket;
contracting said deformable jacket by sliding said first catheter relative to said second catheter to increase said distance;
maneuvering said declotter with said guidewire;
positioning said declotter adjacent said site; and
expanding said deformable jacket by sliding said first catheter relative to said second catheter to decrease said distance to declot said site.

42. The method of claim 41, further comprising preventing material from entering an interior of said declotter with said liner.

43. The method of claim 41, further comprising continuously modifying a diameter of said deformable jacket by sliding said first catheter relative to said second catheter.

44. The method of claim 41, wherein said site is an thrombosed hemodialysis access graft site.

45. The method of claim 41, wherein said site is a thrombosed intragraft site.

46. The method of claim 41, wherein said site is a venous stenosis site.

* * * * *

UNITED STATES PATENT AND TRADEMARK OFFICE
CERTIFICATE OF CORRECTION

PATENT NO.   :   6,146,396

DATED        :   November 14, 2000

INVENTOR(S)  :   Konya, et al

It is certified that error appears in the above-identified patent and that said Letters Patent is hereby corrected as shown below:

At Column 19, Claim 24, delete the word "lease" and insert therefor the word -- least --.

Signed and Sealed this

Twenty-ninth Day of May, 2001

*Attest:*

NICHOLAS P. GODICI

*Attesting Officer*       *Acting Director of the United States Patent and Trademark Office*